US 8,708,493 B2

(12) United States Patent
Reimer et al.

(10) Patent No.: US 8,708,493 B2
(45) Date of Patent: Apr. 29, 2014

(54) ILLUMINATION DEVICE AS WELL AS OBSERVATION DEVICE

(75) Inventors: Peter Reimer, Ellwangen (DE); Heinz Abramowsky, Geigen (DE); Daniel Kolster, Oberkochen (DE); Fritz Straehle, Heubach (DE); Alfons Abele, Schwaebisch-Gmuend (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 12/803,484

(22) Filed: Jun. 28, 2010

(65) Prior Publication Data

US 2011/0037947 A1   Feb. 17, 2011

Related U.S. Application Data

(62) Division of application No. 11/659,594, filed as application No. PCT/EP2005/007803 on Jul. 18, 2005, now Pat. No. 8,177,364.

(30) Foreign Application Priority Data

Aug. 6, 2004   (DE) .......................... 10 2004 038 372
Oct. 18, 2004  (DE) .......................... 10 2004 050 651

(51) Int. Cl.
*A61B 3/10* (2006.01)
*A61B 3/12* (2006.01)

(52) U.S. Cl.
CPC ................. *A61B 3/1225* (2013.01); *A61B 3/12* (2013.01)
USPC .......................................... 351/221; 351/205

(58) Field of Classification Search
USPC .......... 359/385, 387, 389; 351/205, 206, 214, 351/221
See application file for complete search history.

(56) References Cited

U.S. PATENT DOCUMENTS

| 3,850,527 | A | * | 11/1974 | Winthrop et al. | ............. 356/129 |
| 5,243,368 | A | * | 9/1993 | Ito et al. | ......................... 351/221 |
| 5,619,372 | A | * | 4/1997 | Hellmuth et al. | ............. 359/389 |
| 2004/0174591 | A1 | * | 9/2004 | Sander | ........................... 359/388 |

* cited by examiner

*Primary Examiner* — Mahidere Sahle
(74) *Attorney, Agent, or Firm* — Kriegsman & Kriegsman

(57) ABSTRACT

Disclosed are an illumination device for an observation device comprising one, two or more observation beam paths with one respective beam of observation rays, especially for an ophthalmologic surgical microscope, and a corresponding observation device. Said illumination device is provided with at least one light source for generating at least one beam of observation rays in order to illuminate an object that is to be observed. According to one embodiment of the invention, at least two partial bundles of illumination rays are provided, each of which extends coaxial to a corresponding beam of observation rays, while the partial beams of illumination rays are embodied so as to form two or several illumination spots on the fundus of an object that is to be observed, e.g. an eye, said illumination spots having variable sizes, thus allowing the illumination beam to cooperate in a precisely defined manner with the observation beam paths, which makes it possible to meet especially the practical requirements regarding homogeneity of the red reflex.

8 Claims, 4 Drawing Sheets

HB = Principal observer (PO)   MB = Co-observer (CO)

ILLUMINATION DEVICE AS WELL AS OBSERVATION DEVICE

CROSS-REFERENCE TO RELATED APPLICATIONS

The present application is a divisional of U.S. patent application Ser. No. 11/659,594, inventors Peter Reimer et al., filed Feb. 6, 2007, now U.S. Pat. No. 8,177,364 the disclosure of which is incorporated herein by reference.

BACKGROUND OF THE INVENTION

The present invention relates first to an illumination device for an observation device having one, two or more observation beam paths, having an observation light bundle for each path, having a least one light source for producing at least one illumination light bundle for illuminating an object to be observed, in particular, an eye to be observed, wherein at least two partial illumination light bundles are provided and wherein each partial illumination light bundle runs coaxially to a corresponding observation light bundle and also relates to an illumination device for an observation device having one, two or more observation beam paths, having an observation light bundle for each path, having at least one light source for producing at least one illumination light bundle for illuminating an object to be observed, in particular, an eye to be observed. In addition, the invention relates to an observation device, in particular, an operating microscope, having one, two or more stereoscopic observation beam paths, having an observation light bundle for each path, and having an illumination device, having at least one light source for producing at least one illumination light bundle for illuminating an object to be observed, in particular, an eye to be observed, wherein at least two partial illumination light bundles are provided and wherein each partial illumination light bundle runs coaxially to a stereoscopic observation light bundle and also relates to an observation device, in particular, an operating microscope, having one, two or more stereoscopic observation beam paths, having an observation light bundle for each path, and having an illumination device, having at least one light source for producing at least one illumination light bundle for illuminating an object to be observed, for example, an eye. In addition, the invention relates to the use of the above illumination device in an operating microscope, in particular, in an ophthalmologic observation device, preferably in an operating microscope designed for cataract extraction and to the use of the above observation device as an operating microscope, in particular, as an ophthalmologic observation device, preferably as an operating microscope designed for cataract extraction.

For example, an observation device may involve an operating microscope. In particular, the observation device can be designed as an ophthalmologic operating microscope, which is utilized, for example, for a special application in eye surgery, i.e., cataract surgery.

In the case of cataract surgery, a lens of the eye—which is clouded, for example, due to the cataract—is replaced by an artificial lens.

The lens of an eye is found inside a thin envelope, the so-called lens capsule. In order to remove the lens of the eye, access to it is created by a thin cut made in the lens capsule and the lens of the eye is first broken up into small pieces with a microsurgical instrument, and then these pieces are removed by means of an aspirating device.

This process takes place under microscopic observation—for example, under stereomicroscopic observation—employing a specially designed illumination device for such interventions. This illumination device presents both an illumination of the surrounding field, which is necessary for illuminating the entire operating field, as well as a red background illumination for the actual operating field limited to the pupil region of the lens of the eye, which is of decisive importance for the cataract operation. This red background illumination is derived from the fraction of illuminating light, which, after passing through the transparent media of the eye, finally strikes the retina, which appears red due to good blood perfusion, is back-scattered therefrom, and then can be observed, of course, as an apparent red background illumination by the surgeon also by means of the operating microscope. This very characteristic red background illumination in cataract surgery is generally known in the profession under the term "red reflex".

For an optimal recognition of details relevant to the cataract operation, a red background illumination that is as homogeneous as possible has been proven to be a necessary prerequisite for the surgeon. A first requirement of the illumination device is thus to assure a homogeneity of the red reflex that is as optimal as possible over the entire pupil of the patient.

For complete elimination of the pieces of the lens of the eye which has been broken up into tiny pieces and for good recognition of transparent membranes, for example, of the lens capsule, another requirement must be fulfilled, that is, there must be a good contrasting of phase objects and in fact, this contrast should also be provided as much as possible over the entire pupil of the patient.

In the past, various solutions have already been made known in connection with the production of such red background illumination.

In U.S. Pat. No. 4,779,968, a coaxial illumination for an operating microscope is described. According to this solution, a lighting module is provided, which can be subsequently incorporated as an additional module in existing operating microscopes. This additional module is preferably introduced on the object side underneath the principal objective of the observation device. The illumination is coupled onto the axis of the microscope either with a beam-splitter plate or a beam-splitter cube.

An illumination device for an operating microscope is described in DE 4,028,605 C2, which permits a combination of zero-degree, coaxial and oblique illumination. For this purpose, the illumination device makes available movable sub-mirrors as well as a stationary six-degree mirror plus the respective variable diaphragms, by which means the angle of illumination and the lighting components of the respective illumination device can be varied. The emphasis of this known solution lies in increasing the contrast by means of a coaxial illumination, wherein this coaxial illumination involves an oblique illumination found near the axis.

An ophthalmologic observation device is disclosed in DE 196 38,263 A1, in which the unavoidable corneal reflex that occurs when a patient's eye is illuminated for observation of the front segments of the eye will be suppressed. This is performed by introducing a light absorber in the form of a black point in the vicinity of a luminous-field diaphragm of an otherwise known illumination.

A reversible illumination system for an ophthalmologic operating microscope is described in U.S. Pat. No. 6,011,647, in which the system can be switched between a surrounding-field illumination and an optimized "red reflex" illumination during the operation. The illumination device is comprised of a light source, a collector, a luminous-field diaphragm, a tilting mirror, a field lens and a principal objective. In the case of this optimized "red reflex" illumination, the helix of the light source is then imaged or mapped in the pupil of the eye as the object plane, and not the luminous-field diaphragm as is the case with surrounding-field illumination.

In EP 1,109,046 A1, an illumination device for an operating microscope is disclosed, which has two reflection elements that can be moved independent of one another, by means of which both the angle of the incident light with the optical axis of the microscope objective as well as the intensity of the different light beams can be changed independent of one another.

For surgery on the eye, and here, in particular, in cataract operations, a homogeneous, bright "red reflex" is required along with a good contrasting of phase objects over the entire region of the patient's pupil.

The operating microscopes of the prior art fulfill these requirements for regions of the pupil that are of varying size. A compromise must always be found between the primary requirements of a good, homogeneous "red reflex" and a good contrasting of phase objects.

For the most part, illumination is produced at a small angle for observation. This has the consequence, however, that the "red reflex" does not appear uniformly bright over the patient's pupil. An illuminating angle between 2 and 4 degrees has previously proven favorable. At this angle, one obtains a good compromise between good contrasting and illumination of the patient's pupil. With this arrangement, however, the "red reflex" reacts sensitively to a rolling of the patient's eye during the operation.

Tests with coaxial illumination in fact led to a good, homogeneous "red reflex", but to a poor contrasting of phase objects, and thus previously have not proven suitable in practice. In this case, the illuminating optics were disposed such that an illuminating mirror (or prism) lay between the two beam paths of the stereomicroscope. In this case, therefore, a precise 0° illumination, which is accurately produced from the same direction as the observation, was not provided.

Finally, an illumination device for operating microscopes is described in DE 4,417,273 A1, in which the illuminating light bundle is divided into at least two partial illuminating light bundles, wherein each partial illuminating light bundle of the illuminating beam runs coaxially to an illuminating light bundle. In this way, the "red reflex" will be improved.

SUMMARY OF THE INVENTION

Starting from the named prior art, the object of the present invention is to further develop an illumination device as well as an observation device of the type named initially, in order to further improve the desired optimizing. In particular, an illumination device as well as an observation device will be provided, with which an optimal solution to the problem of practical requirements can be provided relative to homogeneity of the "red reflex" and/or good contrasting of the lens pieces or membranes, respectively, in the lens capsule.

According to the invention, this object is solved by an illumination device for an observation device having one, two or more observation beam paths, having an observation light bundle for each path, having at least one light source for producing at least one illumination light bundle for illuminating an object to be observed, in particular, an eye to be observed, wherein at least two partial illumination light bundles are provided and wherein each partial illumination light bundles runs coaxially to a corresponding observation light bundle, hereby characterized in that the partial illumination light bundle are/will be structured in such a way that they form two or more lighting spots that are variable in size on the fundus of an object to be observed. This object is also solved by an illumination device for an observation device having one, two or more observation beam paths, having an observation light bundle for each path, having at least one light source for producing at least one illumination light bundle for illuminating an object to be observed, in particular, an eye to be observed, hereby characterized in that the illumination light bundle is imaged in a diffraction-limited manner and that the illumination light bundle forms one or more lighting spots that are variable in size on the fundus of the object to be observed. This object is additionally solved by an illumination device for an observation device having one, two or more observation beam paths, having an observation light bundle for each path, having at least one lieht source for producing at least one illumination light bundle for illuminating an object to be observed, in particular, an eye to be observed, hereby characterized in that the size of the lighting spot(s) on the fundus of the object to be observed does not exceed 1 X, preferably 0.7 X, more preferably 0.5 X, most preferably 0.3 X of the cross-sectional area of the observation light bundle on the fundus. Moreover, this object is solved by an observation device, in particular, an operating microscope, having one, two or more stereoscopic observation beam paths, having an observation light bundle for each path, and having an illumination device, having at least one light source for producing at least one illumination light bundle for illuminating an object to be observed, in particular, an eye to be observed, wherein at least two partial illumination light bundles are provided and wherein each partial illumination light bundle runs coaxially to a stereoscopic observation light bundle, hereby characterized in that the partial illumination light bundles are/will be formed in such a way that they form two or more lighting spots that are variable in size on the fundus of an object to be observed. This object is also solved by an observation device, in particular, an operating microscope, having one, two or more stereoscopic observation beam paths, having an observation light bundle for each path, and having an illumination device, having at least one light source for producing at least one illumination light bundle for illuminating an object to be observed, for example, an eye, hereby characterized in that the illumination light bundle is imaged in a diffraction-limited manner and that the illumination light bundle forms one or more lighting snots that are variable in size on the fundus of the object to be observed. This object is additionally solved by an observation device, in particular, an operating microscope, having one, two or more stereoscopic observation beam paths, having an observation light bundle for each path, and having an illumination device, having at least one light source for producing at least one illumination light bundle for illuminating an object to be observed, for example, an eye, hereby characterized in that the illumination light bundle forms at least one lighting spot on the fundus of the object to be observed and that the size of the lighting spot(s) on the fundus does not exceed 1 X, preferably 0.7 X, more preferably 0.5 X, most preferably 0.3 X of the cross-sectional area of the observation light bundle on the fundus. Furthermore, this object is solved by the use of an illumination device as disclosed herein in an operating microscope, in particular, in an ophthalmologic observation device, preferably in an operating microscope designed for cataract extraction and by the use of an observation device as disclosed herein as an operating microscope, in particular, as an ophthalmologic observation device, preferably as an operating microscope designed for cataract extraction. Other advantages, features, details, aspects and effects of the invention result from the subclaims, the description, as well as the drawings. Features and details that are described in connection with the illumination device according to the invention, thus also apply, obviously, in connection with the observation device according to the invention and vice versa. The same is true for the particular uses.

According to the first aspect of the invention, an illumination device is provided for one, two or more—particularly stereoscopic—observation beam paths, with an observation device having an observation light bundle for each path, having at least one light source for producing at least one illumination light bundle for illuminating an object to be observed, in particular, an eye to be observed, wherein at least two partial illumination light bundles are provided and wherein each partial lighting illumination bundle runs coaxially to a corresponding observation light bundle. The illumination device is hereby characterized according to the invention in that the partial illumination light bundles are/will be formed in such a way that they form two or more lighting spots that are variable in size on the fundus of an object to be observed, for example, an eye.

The essence of the present invention thus first lies in a new conception of the illumination device. The new conception of the illumination device, among other things, consists of the fact that the latter produces at least two light bundles originating from one or even several light sources, wherein the optical axes of these light bundles run coaxially to the optical axes of the observation light bundles.

For example, a single light source can be provided, which first produces a single illumination light bundle. This illumination light bundle is subsequently divided into the desired number of partial illumination light bundles by suitable means, for example, beam splitters or the like. For example, it may also be provided, however, that the illumination device has two or more light sources, wherein each light source then produces one partial illumination light bundle.

In this way, a true coaxial illumination is created. "Coaxial" is therefore generally an illumination near the axis. This includes both an illumination under precisely zero degree as well as an oblique illumination at a very small angle near the axis. This could be denoted as "substantially coaxial". Examples of this are explained in more detail in the further course of the description.

The new illumination concept of at least two coaxial partial illumination light bundles, according to the invention, produces two or more lighting spots that are variable in size on the fundus of the object to be observed, for example, an eye.

The invention is not limited to a specific size or shape of the lighting spots. Advantageously, the lighting spots can have a round or approximately round geometry. Other geometries are also conceivable, however, i.e., elliptical, polygonal, annular lighting spots and similar shapes.

Then, in addition to a homogeneous "red reflex", a good contrasting of phase objects is also obtained by a neat, diffraction-limited imaging of the (secondary) light source onto the fundus.

Advantageously, the diameter of the lighting spots can be varied in a range between 0.5 and 1.5 mm on the fundus of the object to be observed. Of course, the lighting spots may also have a larger or smaller diameter. Advantageously, the diameter of the lighting spot(s) can be formed such that it does not exceed 1.5 mm, preferably 1.0 mm, and more preferably 0.5 mm, on the fundus of the object to be observed.

The variation in the diameter of the lighting spot is thus caused by a variation of the partial illumination light bundle.

Advantageously, the illumination light bundles can be/will be able to be formed such that the size of the lighting spot on the fundus of the object to be observed does not exceed 1×, preferably 0.7×, more preferably 0.5×, most preferably 0.3× of the cross-sectional area of the observation light bundle on the fundus.

The variation of the diameter of the lighting spot can be produced in different ways. Advantageously, this is done with the help of diaphragms, for example discrete diaphragms with different diameters or variable diaphragms with variable diameters (iris diaphragms). It is also conceivable, however, to utilize suitable displays for this purpose, for example, LCD displays. Likewise, it is possible to produce variation by means of a suitable zoom system. The last-named variant has the additional advantage that the light intensity increases in the lighting spot, if the diameter of the lighting spot is made smaller.

The intensity (brightness) and the homogeneity of the "red reflex" can be influenced by the variation of the lighting spot on the fundus of an object to be investigated. The greater the diameter is selected for the lighting spot, the more homogeneous and brighter is the "red reflex". The smaller the diameter is selected for the lighting spot, the better is the contrasting of the "red reflex". The suitable diameter of a lighting spot is now freely adjustable, depending on need and case of application each time.

With an illumination device according to the present invention, a precise coaxial illumination is produced, which supplies a homogeneous "red reflex", and which is also still insensitive to a rolling of the object to be observed, for example, a patient's eye. In this way, a possible readjustment of the illumination for optimizing the "red reflex" when the eye rolls can also be dispensed with, whereby the construction of the illumination device or of a corresponding observation device is simplified.

According to the invention, the illumination device is provided for an observation device, but the invention is not limited to specific types of observation devices. For example, but not exclusively, however, the observation device may involve an operating microscope. Several non-exclusive examples for possible application purposes in the field of operating microscopes are described in detail in connection with the observation device according to the invention.

Particularly advantageously, the illumination device according to the invention can be utilized as a 0° illumination system—in particular, a dual system—for an operating microscope for application in ophthalmic surgery.

According to an advantageous configuration, each partial illumination light bundle is guided in such a way that an object to be observed is/will be illuminated from the same direction, with respect to each observation light bundle, from which the observation is also produced (0° observation). If the observation device involves a (stereo) operating microscope, each partial illumination light bundle is guided in such a way that the object to be observed—for example, an eye—is illuminated from the same direction from which the observation is also made, for the left and right observation beam paths of the (stereo) operating microscope. Therefore, a precise 0° illumination is present for each observation beam path.

According to another advantageous configuration, each partial illumination light bundle is guided in such a way that an object to be observed relative to each observation light bundle is/will be illuminated obliquely at an angle of less than/equal to 2 degrees, preferably less than/equal to 1 degree (oblique illumination near the axis). The object to be investigated will be illuminated at a small angle for observation.

An optimal "red reflex" with simultaneous good contrasting is obtained by a neat, diffraction-limited guidance of the light beam for the illumination and small lighting spots on the fundus of a patient's eye. Further, this illumination device reacts very non-critically to a rolling of the patient's eye during the operation.

A particularly advantageous embodiment of the invention provides an illumination device for one, two or more observation beam paths, with an observation device having an observation light bundle for each path, with at least one light source for producing at least one illumination light bundle for illuminating an object to be observed, in particular, an eye to be observed, whereby each observation light bundle or partial observation light bundle, respectively, runs coaxially or at least substantially coaxially to the corresponding observation light bundle, whereby the size of the lighting spot(s) on the fundus of the object to be observed does not exceed 1×, preferably 0.7×, more preferably 0.5×, most preferably 0.3× of the cross-sectional area of the observation light bundle on the fundus. In an advantageous enhancement, it can be further provided that the diameter of the lighting spot(s) on the fundus does not exceed 1.5 mm, preferably 1.0 mm, and more preferably 0.5 mm.

According to another aspect of the invention, an illumination device is provided for an observation device having one, two or more stereoscopic observation beam paths, with an observation light bundle for each path, having at least one light source for producing at least one illumination light bundle for illuminating an object to be observed, in particular, an eye to be observed. The illumination device is characterized according to the invention in that the illumination light bundle is imaged in a diffraction-limited manner and that the illumination light bundle forms one or more lighting spots that are variable in size on the fundus of the object to be observed.

In the simplest case, according to this aspect, a single illumination light bundle is provided, which produces a single lighting spot. Embodiments having two or more illumination light bundles are also possible, however, whereby in each case, one illumination light bundle produces one lighting spot. In the last-named case, the illumination light bundles—when considered in their totality—each represent a partial illumination light bundle.

For the configuration of the illumination device according to the invention, reference is also made to the preceding embodiments for the first aspect of the invention.

It can be advantageously provided that the size of the lighting spot(s) on the fundus of the object to be observed does not exceed 1×, preferably 0.7×, more preferably 0.5×, most preferably 0.3× of the cross-sectional area of the observation light bundle on the fundus.

According to another aspect, an illumination device is provided for an observation device having one, two or more observation beam paths, with an observation light bundle for each path, having at least one light source for producing at least one illumination light bundle for illuminating an object to be observed, in particular, an eye to be observed. It can be provided according to the invention that the size of the lighting spot(s) on the fundus of the object to be observed does not exceed 1×, preferably 0.7×, more preferably 0.5×, most preferably 0.3× of the cross-sectional area of the observation light bundle on the fundus.

Advantageously, at least one illumination light bundle may run coaxially to the corresponding observation light bundle.

In another configuration, it is advantageously provided that the distance of the center of the lighting spot from the center of the cross-sectional area of the observation light bundle on the fundus amounts to 0.8×, preferably 0.5×, more preferably 0.2×, most preferably 0.05× of the radius of the cross-sectional area of the observation light bundle on the fundus.

By the illumination device according to the present invention, it can be achieved, in particular, that the optimal size of the lighting spot is aligned to the refractive error of the patient and the magnification of the observation device, for example, an operating microscope. This is achieved, for example, by the relative data of the size of the lighting spot relative to the cross-sectional area of the observation light cone on the fundus. The essential features for an optimal red reflex are realized, i.e., small spot size for good contrast, as well as the position of the lighting spot on the fundus.

An advantageous embodiment of the invention provides an illumination device for an observation device having one, two or more observation beam paths, having an observation light bundle for each path, having at least one light source for producing at least one illumination light bundle for illuminating an object to be observed, in particular, an eye to be observed, whereby the size of the lighting spot(s) on the fundus of the object to be observed does not exceed 1×, preferably 0.7×, more preferably 0.5×, most preferably 0.3× of the cross-sectional area of the observation light bundle on the fundus, and whereby the distance of the center of the lighting spot from the center of the cross-sectional area of the observation light bundle on the fundus amounts to 0.8×, preferably 0.5×, more preferably 0.2×, most preferably 0.05× of the radius of the cross-sectional area of the observation light bundle on the fundus.

Advantageously, the diameter of the at least one lighting spot can be varied in a range between 0.5 and 1.5 mm on the fundus of the object to be observed. Advantageously, the diameter of the lighting spot(s) can be formed such that it does not exceed 1.5 mm, preferably 1.0 mm, and more preferably 0.5 mm on the fundus of the object to be observed.

Advantageously, the illumination device according to the invention can have at least one objective element. The objective element can also be formed as an objective element of an observation device, in particular as its principal objective. However, this is not absolutely necessary.

In addition, different optical elements, which are disposed between the at least one light source and the at least one objective element, can be provided in the illumination device.

In an advantageous configuration, means are provided in order to superimpose an observation light bundle on a partial illumination light bundle or, respectively, the illumination light bundle. These means can be configured in the most diverse way and disposed at the most diverse sites. Several nonexclusive examples will be explained below for this purpose.

For example, it may be provided that the means for superimposing are disposed in such a way that a superimposition of the observation light bundle on a partial illumination light bundle or the illumination light bundle is made above the objective element. The superimposition of the observation light bundle on a partial illumination light bundle or the illumination light bundle can be made, for example, in the parallel beam path above the principal objective.

For example, it may be provided that the means for superimposing are disposed in such a way that a superimposition of the observation light bundle on a partial illumination light bundle or the illumination light bundle is made underneath the objective element. The possibility thus also exists of superimposing a partial illumination light bundle or the illumination light bundle, respectively, on the observation light bundle underneath the principal objective. It is advantageous in this case, if the partial illumination light bundles are inclined, corresponding to the focal depth of the principal objective.

Advantageously, it may be particularly provided in the last-named case that the objective element is formed as a so-called varioscope optics. A varioscope optics generally involves an optics with at least two optical elements separated by a distance, wherein the free working distance between objective and object plane can be varied by variation of this distance. Such a varioscope optics is already known in and of itself from the prior art. In the above-described case, with superimposition of the light bundles underneath the objective element, it is advantageous, when a varioscope optics is used, if the partial illumination light bundles are re-adjusted corresponding to the free working distance.

As has been stated above, the invention is not limited to specific types of configurations of "superimposition means". For example, the means for superimposing can have at least one optical element in the form of a prism and/or a beam splitter plate and/or a mirror, e.g., a semi-reflecting mirror and/or a perforated mirror. Of course, the means can be configured in another way, so that the invention is not limited to the named examples.

In another configuration, it can be provided that means are provided in order to produce at least one annular partial illumination light bundle, which is disposed around an observation light bundle.

Advantageously, at least one device for changing the cross section of the bundle of the at least one illumination light bundle and/or at least one partial illumination light bundle can be provided. In such a case, the invention is not limited to specific embodiments of the device. The device can be designed, for example, as a diaphragm, in particular, an iris diaphragm or a discrete diaphragm, as an LCD (liquid crystal display) display, as a DMD (digital mirror device), as an LCOS (liquid crystal on silicon), as an FLCOS (ferroelectric liquid crystal on silicon), or similar device. By incorporating an appropriate device in the illumination device, e.g., in the illumination beam, it is possible to vary the light spot on the surface of the object to be observed, for example, on the fundus of the patient's eye. A small light spot supplies a better contrast. In cataract surgeries, it may be the case that the "red reflex" can appear too dark, particularly in the case of dense cataracts. Here, it is of advantage to enlarge the light spot and thus increases the brightness. The intensity of the radiation on the retina will not be increased thereby. Negative effects on contrast are not to be expected, since in the case of a very dense or thick cataract, the light spot is scattered without anything further.

Another advantage of the illumination device according to the invention consists of the fact that only a corneal reflex will be visible on the cornea-front surface of the patient's eye, since the partial illumination light bundles are approximately overlapped or masked at this site.

In an advantageous configuration, it can be provided that two or more light sources are provided and that a partial illumination light bundle will be produced by means of each light source. Thus independent light sources can be used, whereby each light source produces its own partial illumination light bundle.

In another advantageous configuration, it can be provided that a single light source is provided and that means for splitting the illumination light bundle of the light source into two or more partial illumination light bundles are provided. Here, suitable beam splitters in the form of prisms, semi-reflecting mirrors and similar means can be used.

The present invention is not limited to the use of specific light sources. Several nonexclusive, advantageous examples will be named below for this purpose. For example, the at least one light source can be formed as a lamp, in particular as a halogen lamp or a xenon lamp, as a laser, as a non-thermal radiator, as a light guide, in particular as an optical-fiber light guide bundle, as at least one LED (light-emitting diode), as at least one OLED (organic light-emitting diode), or similar source. Of course, combinations of different light sources are also possible.

Advantageously, the light source is formed of an arrangement of one or more micro light source(s) that can be switched on individually or by regions. The illumination device is configured such that it can be varied in a simple manner with respect to the geometry of the light field that it produces. In this way, the micro light sources will be controlled—in particular, electronically—from the outside, preferably by a control device. Another feature provides that the micro light sources can be controlled, at least in regions, in order to be able to adjust variable lighting geometries. This is particularly of advantage in the case of the generation of annular partial illumination light bundles. In this case, the invention is not limited to specific sizes and/or shapes of regions. In the simplest case, a single point can be controlled in such a way. Particularly when the luminous source is formed from a matrix comprised of individual micro light sources, one or more micro light sources can be controlled individually or in groups, whereby in the last-named case, individual micro light sources can be combined into one region. Also, in this respect, the invention is not limited to concrete configurations.

Advantageously, the light source can be formed of an arrangement of one or more light diode(s) (LEDs), in particular organic light diode(s) (OLEDs). Organic light diodes were originally developed as microdisplays. Unlike LCDs, which require a backlighting, OLEDs by themselves illuminate as Lambert radiators (surface or flat emitters).

As patterned lighting sources, OLEDs offer a good light efficiency and small structures without intermediate dark spaces. Depending on the desired lighting geometry, individual micro light sources can be turned on and others can be turned off. The filling factor is higher in OLEDs as opposed to LEDs, which means that a higher packing density can be realized. The use of a display of LEDs or OLEDs makes possible a programmable, and also, for example, an automatable switching of different lighting modes, without having to move mechanical components, such as, e.g., phase contrast rings, filters, reducers and similar components. Particularly suitable, for example, are white OLEDs, whose spectrum is determined by a mixture of organic molecules.

In summary, the illumination device described above has a large number of advantages. A very homogeneous and bright "red reflex" can be produced by a coaxial lighting, in particular by a "true" 0° illumination. The "red reflex" reacts very insensitively to a tilting of the object to be observed, for example a patient's eye. That is, a readjustment relative to angles can be dispensed with. By integrating a device for changing the cross section of the light bundle, for example, a (double) iris diaphragm, the brightness of the "red reflex" and the contrast of phase structures can be adapted and optimized to the treatment situation. The contrast will be improved by reducing the diameter of the iris diaphragm, but, of course, the brightness will also decrease.

According to another aspect of the invention, an observation device is provided, in particular an operating microscope, having one, two or more stereoscopic observation beam paths, having an observation light bundle for each path, and having an illumination device, having at least one light source for producing at least one illumination light bundle for illuminating an object to be observed, in particular, an eye to be observed. The illumination device has—adapted to stereoscopic observation—at least two partial illumination light bundles, wherein each partial illumination light bundle runs coaxially to a stereoscopic observation light bundle. According to the invention, it is provided that the partial illumination light bundles are formed in such a way that they form two or more lighting spots that are variable in size on the fundus of an object to be observed.

According to another aspect of the invention, an observation device is provided, in particular an operating microscope, having one, two or more stereoscopic observation beam paths, having an observation light bundle for each path, and having an illumination device, having at least one light source for producing at least one illumination light bundle for illuminating an object to be observed, for example, an eye. This observation device is hereby characterized according to the invention in that the illumination light bundle is imaged in a diffraction-limited manner and that the illumination light bundle forms one or more lighting spots that are variable in size on the fundus of the object to be observed.

According to another aspect of the invention, an observation device is provided, in particular an operating microscope, having one, two or more stereoscopic observation beam paths, having an observation light bundle for each path and having an illumination device, having at least one light source for producing at least one illumination light for illuminating an object to be observed, for example, an eye. This observation device is hereby characterized according to the invention in that the illumination light bundle forms at least one lighting spot on the fundus of the object to be observed and that the size of the lighting spot(s) on the fundus does not exceed 1 X, preferably 0.7×, more preferably 0.5×, most preferably 0.3× of the cross-sectional area of the observation light bundle on the fundus.

Advantageously, the diameter of the at least one lighting spot can vary in a range between 0.5 and 1.5 mm on the fundus of the eye to be observed. Advantageously, the diameter of the lighting spot(s) can be formed such that it does not exceed 1.5 mm, preferably 1.0 mm, and more preferably 0.5 mm on the fundus of the object to be observed.

Advantageously, the illumination device is constructed in the way described above, according to the invention, so that reference is made here to the corresponding descriptions.

The observation device may have, for example, a principal objective element, which is identical to an objective element of the illumination device. In addition, means can be provided in order to superimpose an observation light bundle on a partial illumination light bundle or, respectively, the illumination light bundle. The means for superimposing can be disposed in such a way that a superimposition of the observation light bundle on a partial illumination light bundle or the illumination light bundle, respectively, is made above the principal objective element.

In another configuration, it may be provided that the observation device has a principal objective element that is identical to an objective element of the illumination device, that means are provided in order to superimpose an observation light bundle on a partial illumination light bundle or, respectively, an illumination light bundle and that the means for superimposing are disposed in such a way that a superimposition of the observation light bundle on a partial illumination light bundle or the illumination light bundle, respectively, is made underneath the principal objective element.

For the last-named case, it may be advantageously provided that the principal objective element is formed as a so-called varioscope optics. For the configuration and mode of operation of the varioscope optics, reference is made to the corresponding description given above in connection with the illumination device according to the invention.

Advantageously, the observation device can be formed as a stereoscopic observation device, in particular as a stereomicroscope. The optical system of an operating microscope basically consists of several structural elements, such as the tube, the basic body of the microscope, etc. Additionally, it is possible in many operating microscopes to connect various additional modules, such as, for example, a co-observer tube for an assistant observer, a video camera for documentation or similar units.

Several assemblies can also be combined inside the base body of the microscope, such as, for example, an illumination device, a magnification device, the principal objective, or similar components. The characteristic dimension for the principal objective is its focal depth, which establishes the working distance from the operating microscope to the surgical field and also has an influence on the total magnification of the microscope.

Preferably, a magnification system can be provided in the at least one observation beam path. For example, this may involve a magnification changing device, with which different magnifications can be adjusted. In many cases of application, one stepwise magnification change is fully sufficient. However, it is also possible to use pancratic magnification systems as the magnification system, by means of which a step-free magnification (zoom system) is possible. In this way, it may be advantageously provided that the device pupil of the observation device, which has already been described further above, is permanently disposed in the magnification system.

In addition, a tube element and an eyepiece element can be provided in the at least one observation beam path. The task of an eyepiece element is generally the post-magnification of the intermediate image forming in the tube, as well as perhaps compensating for the possible refractive error of the user of such a microscope.

In addition, it is advantageously provided that the object plane of the object to be investigated is formed at the front focal point of the principal objective. It is achieved in this way that the object to be investigated is imaged infinitely by the principal objective.

Advantageously, the observation device can be formed as a stereoscopic observation device, in particular as a stereomicroscope. In this case, the observation device provides two observation beam paths running in parallel.

The observation device may involve a stereomicroscope according to the telescopic principle according to a preferred embodiment, which is essentially comprised of the three optical sub-components, i.e., a principal objective (afocal), a zoom system as well as a binocular telescopic device consisting of tube and eyepiece.

The observation light bundles run between the individual sub-components of the observation device, preferably in parallel, so that the individual sub-components can be exchanged and combined in modular manner.

In a preferred way, an illumination device according to the invention as described above can be used in an operating microscope, in particular in an ophthalmologic observation device, preferably in an operating microscope designed for cataract extraction. Likewise, an observation device according to the invention as described above can be used as an ophthalmologic observation device, preferably as an operating microscope configured for cataract extraction.

According to the present invention, in particular, the basic requirements in principle have been established for an optimized illumination system in cataract surgery, i.e., a coaxial illumination for homogeneity of the red reflex, and a stigmatic, diffraction-limited imaging of the well-defined lighting spot for good contrasting of the red reflex.

For example, a prism system is proposed for producing the coaxial illumination light bundles. The size of the lighting spot on the fundus can be adjusted in a targeted manner by suitable adaptation of aperture diaphragms in the prism system.

In addition, the illumination system according to the invention permits a simple switching between the optimized red reflex illumination and the surrounding-field illumination that can be indispensable for practical application, for complete illumination of the maximum visual field for stereoscopic observation.

BRIEF DESCRIPTION OF THE DRAWINGS

The invention will now be explained in more detail based on embodiment examples with reference to the attached drawings. Here.

DETAILED DESCRIPTION OF THE INVENTION

Figure 1:
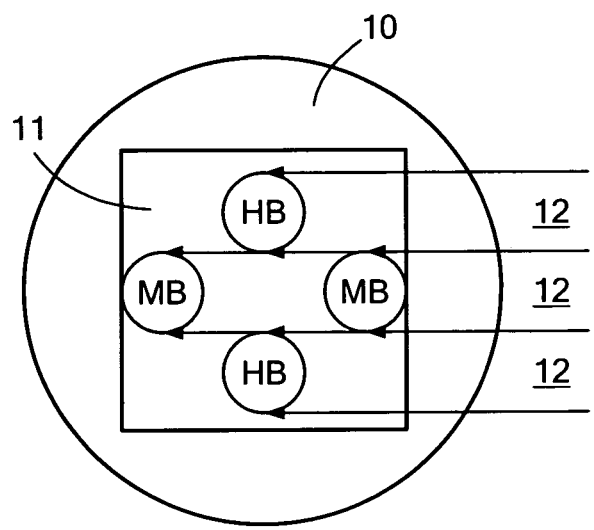
FIG. 1 shows in schematic representation one possible arrangement for producing a 0° illumination, with simultaneous optimal "red reflex" and good contrasting.
Figure 1:
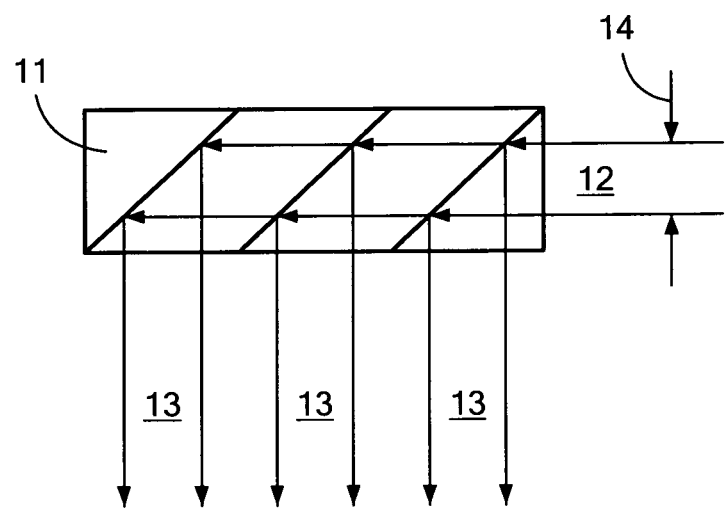

Parts of an illumination device, which is utilized in an observation device, are shown in FIG. 1. The observation device involves a stereo operating microscope for use in ophthalmic surgery, for example, for conducting cataract operations. A very uniform, bright "red reflex" is obtained by means of the illumination device by splitting the illumination light bundle 12 into several partial illumination light bundles 13. This is performed by means 11 for splitting the illumination light bundle, which may provide a suitable mirror/prism arrangement for this purpose. The partial illumination light bundles 13 are thus guided in such a way that the object to be observed, in the present case, a patient's eye, is illuminated from the same direction from which the observation is also produced (0° illumination), relative to the left and right observation beam paths of the operating microscope.

As can be taken from the left-hand side of the figure, observation beam paths both for a principal observer (PO) as well as also for a co-observer (CO) are provided in the example shown. Means 11 for splitting the illumination beam path may be disposed, for example, in the region of an objective element 10, which means may also involve, for example, the principal objective of the observation device.

An optimal "red reflex" with simultaneous good contrasting is obtained with this arrangement by a neat, diffraction-limited guidance of the beam for the illumination and small lighting spots on the fundus of the patient's eye (diameter of approximately 0.5 to 1.5 mm). Further, this lighting arrangement reacts very non-critically to a rolling of the patient's eye during the operation.

The superimposing of the observation light bundle on a partial illumination light bundle 13 can be provided, for example, in the parallel beam path above the objective element 10 (the principal objective) by means 11, which advantageously involves semi-reflecting mirrors or prisms.

Further, a device 14 in the form of an iris diaphragm is provided in the illumination device for changing the cross section of the light bundle. In this way, the luminous spot in the illumination light bundle 12 can be varied on the fundus of the patient's eye.

In the present example, the illumination light bundle 12 is produced by a single light source (not shown) and split into several partial illumination light bundles 13 via means 11. It is also conceivable, however, to use several light sources that are independent of one another, whereby each light source produces at least one partial illumination light bundle 13 each time.

Figure 2:
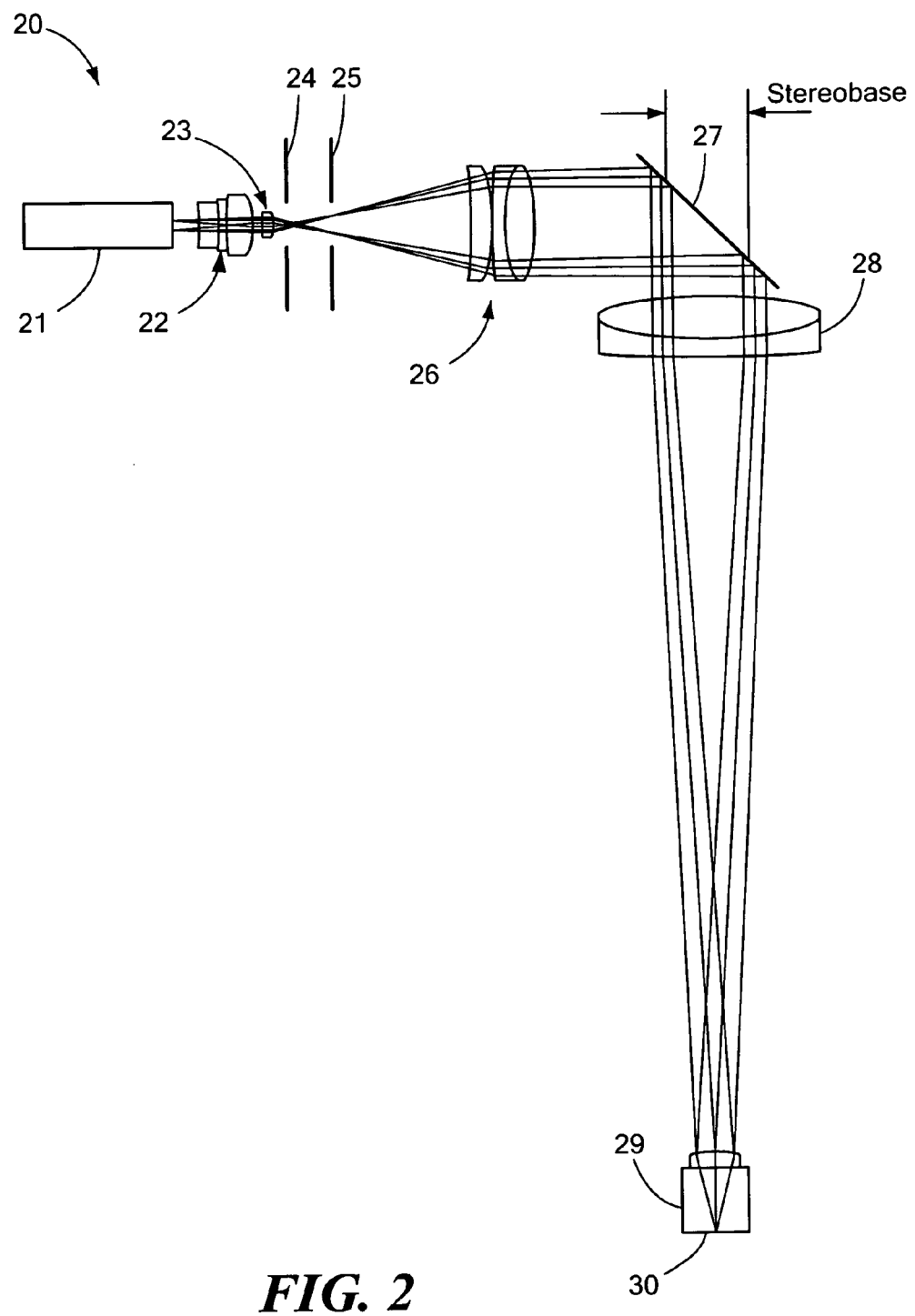
FIG. 2 shows in schematic representation the structure of an optical system for red reflex illumination.

The structure of the optical system for the red reflex illumination is diagrammed in FIG. 2. The following optical components are used, considered starting from a light source in the illumination device 20 which is indicated: a light guide 21, a collector 22, a plano-convex lens 23, a luminous-field diaphragm 24, an aperture diaphragm (pin diaphragm) 25, an optical component 26, for example, a sub-components comprised of a cemented member and meniscus lens, a deflecting element 27, for example, in the form of a separator mirror as well as an objective element 28, for example, in the form of a principal objective. An eye 29 with fundus 30 will be illuminated.

A real intermediate image is produced from the fiber end of light guide 21 with collector 22 and plano-convex lens 23. Aperture diaphragm 25, e.g., in the form of a pin diaphragm, can be introduced at the site of this intermediate image. This real intermediate image lies in the front focal plane of a two-member sub-optics component comprised of the principal objective 28 and the sub-component 26 comprised of a cemented member with meniscus lens. This sub-optics component then forms another virtual intermediate image in infinity, so that, considered from eye 29, the end of the fiber of light guide 21 lies at the far point. Consequently, the fiber end of the light guide 21 is imaged as a lighting spot on the fundus 30 for an eye with correct vision.

The effective luminous area of the fiber end of the light guide 21 may amount to 4.8 mm, for example. The diameter of the intermediate image in the aperture diaphragm 25 then amounts to 5.8 mm. In the named example, a diameter of 1.5 mm is obtained for the size of the lighting spot on fundus 30.

By means of pin diaphragms of well-defined position, the light bundles coaxial to the stereoscopic axes of observation that are necessary for the good homogeneity of the red reflex can be produced in the intermediate image plane (aperture diaphragm), at the distance of the stereo base of the stereoscopic axes of observation. The pin diaphragms are imaged with the same imaging scale factor as the real intermediate image of the end of the fiber, i.e., 5.8:1.5=3.9:1, reduced on the fundus, relative to their position, i.e., lateral displacement to the optical axis, and their size, i.e., diameter of the pin diaphragms. The size of the diameter of the pin diaphragms then determines the size of the lighting spot on the fundus and thus, in a decisive manner, the good contrasting of the red reflex.

The luminous-field diaphragm 24 is found between the plano-convex lens 23 and the real intermediate image of the end of the fiber (aperture diaphragm). This luminous-field diaphragm 24 serves for defining the illuminated visual field.

The luminous-field diaphragm 24 lies at the front focal point of the sub-component 26 comprised of a cemented member and meniscus lens. The luminous-field diaphragm 24 is thus first virtually imaged to infinity on the object plane found at the front focal plane of the principal objective by the sub-component 26, and finally with principal objective 28.

The diameter of the luminous-field diaphragm 24 amounts to 2.5 mm, for example. This leads to an illuminated visual field in the object plane of 10 mm. Therefore, the imaging scale factor amounts to 1:4 for the luminous-field imaging.

The optical system data for the red-reflex illumination are listed in Table 1:

TABLE 1

System data for red-reflex illumination system

| No. | Radius (mm) | Thickness of the light guide (mm) | Medium | Free diameter (mm) |
|---|---|---|---|---|
|   |         | 4.7  | air  |          |
| 1 | −49.759 |      |      | 8.5      |
|   |         | 5.0  | NSK2 |          |
| 2 | −17.655 |      |      | 10.8     |
|   |         | 0.1  | air  |          |
| 3 | −37.047 |      |      | 11.0     |
|   |         | 2.0  | NSF6 |          |
| 4 | 26.227  |      |      | 12.2     |
|   |         | 5.5  | NSK2 |          |
| 5 | −12.589 |      |      | 13.6     |
|   |         | 2.0  | air  |          |
| 6 | 6.6355  |      |      | 5.0      |
|   |         | 2.0  | NSK2 |          |
| 7 | planar  |      |      | 5.0      |
|   |         | 1.9  | air  |          |
| 8 | planar  |      |      | Diaphragm |
|   |         | 13.1 | air  |          |
| 9 | planar  |      |      | Diaphragm |
|   |         | 29.2 | air  |          |
| 10 | −58.984 |     |      | 26.0     |
|   |         | 5.0  | NSK2 |          |
| 11 | −28.387 |     |      | 27.0     |
|   |         | 0.1  | air  |          |
| 12 | 392.42  |     |      | 28.0     |
|   |         | 3.0  | NSF6 |          |
| 13 | 45.316  |     |      | 29.0     |
|   |         | 7.0  | NSK2 |          |
| 14 | −55.033 |     |      | 29.0     |
|   |         | 40.0 | air  |          |
| 15 | planar  |     |      | mirror   |
|   |         | 17.0 | air  |          |
| 16 | 120.57  |     |      | 53.0     |
|   |         | 10.5 | NFK51 |         |
| 17 | −79.719 |     |      | 53.0     |
|   |         | 5.1  | NBAF4 |         |
| 18 | −244.06 |     |      | 53.0     |
|   |         | 188.3 | air |          |
| 19 | 8.0     |     |      |          |
|   |         | 6.0  | BAK4 |          |
| 20 | planar  |     |      | Model eye |
|   |         | 15.4 | BK7  |          |
|   |         |     |      | Fundus   |

Figure 3:
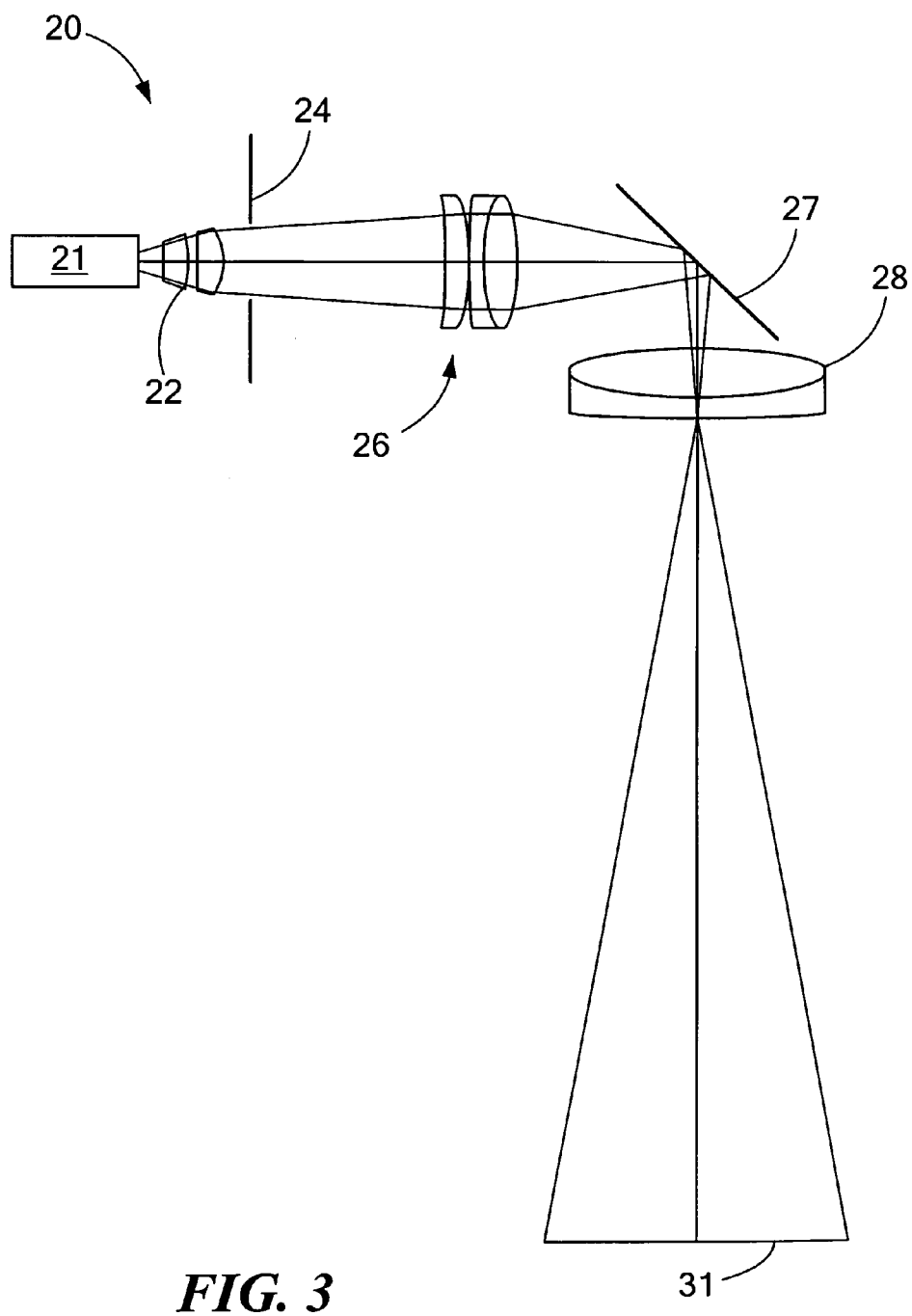
FIG. 3 shows in schematic representation the structure of an optical system for surrounding-field illumination.

The structure of the optical system for the surrounding-field illumination is diagrammed in FIG. 3.

An essential concept consists of the fact that the surrounding-field illumination can be derived by means of a simple switching process from the red-reflex illumination without additional optical components.

Except for the size of the luminous-field diaphragm, the optical components necessary for the surrounding-field illumination are thus identical to the optical components of the red-reflex illumination according to FIG. 2, i.e.: light guide 21, collector 22, luminous-field diaphragm 24, optical component 26, for example, in the form of a sub-component comprised of a cemented member and meniscus lens, deflecting element 27, for example, in the form of a separator mirror as well as objective element 28, for example, in the form of a principal objective.

When switching from red-reflex illumination to surrounding-field illumination, the plano-convex lens and the perforated lens (see FIG. 2) are swung out. In addition, a small luminous-field diaphragm is replaced by a large luminous-field diaphragm 24.

The luminous-field diaphragm 24 is now completely illuminated with collector 22. The luminous-field diaphragm 24 still sits unchanged, as in the case of red-reflex illumination, in the front focal plane of the sub-component 26 comprised of a cemented member and meniscus lens. The luminous-field diaphragm 24 is thus virtually infinitely imaged, so that as in the case of the red-reflex illumination, the image of luminous-field diaphragm 24 again lies in the front focal plane of principal objective 28, by imaging with principal objective 28, and thus lies in the object plane of the observation.

The diameter of the luminous-field diaphragm 24 amounts to 14 mm, for example. Therefore, an illumination of the maximum visual field 31 of approximately 62 mm can be achieved in the object plane. The magnification of the scale factor in comparison to the red-reflex illumination can be clarified by distorting the luminous-field image.

The optical structure for the red-reflex illumination proposed here makes possible an independent engagement in the beam paths for the pupil image and the luminous-field image. Thus, for example, the light power can be optimally adapted to the size of the luminous field, and the size of the lighting spot on the fundus can be adapted by targeted adjustment of the aperture diaphragm.

In the case of surrounding-field illumination, the optical presentation of the problem is reduced on the image of the optimally illuminated luminous-field diaphragm.

Due to the optical structure, for the pupil image, there necessarily results a real intermediate image of the end of the fiber in the vicinity of the front surface of the principal objective. Usually, and also in the case of illumination currently utilized for ophthalmology, this real intermediate image lies in the object space, and in fact, approximately 50 mm underneath the principal objective.

The optical system data for the surrounding-field illumination are listed in Table 2:

TABLE 2

System data for surrounding-field illumination system

| No. | Radius (mm) | Thickness of the light guide (mm) | Medium | Free diameter (mm) |
|---|---|---|---|---|
|   |         | 4.7  | air  |          |
| 1 | −49.759 |      |      | 8.5      |
|   |         | 5.0  | NSK2 |          |
| 2 | −17.655 |      |      | 10.8     |
|   |         | 0.1  | air  |          |
| 3 | −37.047 |      |      | 11.0     |
|   |         | 2.0  | NSF6 |          |
| 4 | 26.227  |      |      | 12.2     |
|   |         | 5.5  | NSK2 |          |
| 5 | −12.589 |      |      | 13.6     |
|   |         | 5.9  | air  |          |
| 6 | planar  |      |      | Diaphragm |
|   |         | 42.3 | air  |          |
| 7 | −58.294 |      |      | 26.0     |
|   |         | 5.0  | NSK2 |          |
| 8 | −28.387 |      |      | 27.0     |
|   |         | 0.1  | air  |          |
| 9 | 392.42  |      |      | 28.0     |
|   |         | 3.0  | NSF6 |          |
| 10 | 45.316 |      |      | 29.0     |
|   |         | 7.0  | NSK2 |          |
| 11 | −55.033 |      |      | 29.0     |
|   |         | 40.0 | air  |          |
| 12 | planar |      |      | mirror   |
|   |         | 17.0 | air  |          |

TABLE 2-continued

System data for surrounding-field illumination system

| No. | Radius (mm) | Thickness of the light guide (mm) | Medium | Free diameter (mm) |
|---|---|---|---|---|
| 13 | 120.57 | | | 53.0 |
| | | 10.5 | NFK51 | |
| 14 | −79.719 | | | 53.0 |
| | | 5.1 | NBAF4 | |
| 15 | −244.06 | | | 53.0 |
| | | 193.6 | air | |
| | | Visual field | | |

It may also be meaningful overall to simultaneous provide the user with red-reflex illumination and surrounding-field illumination. This can be provided, for example, by cementing the plano-convex lens 23 between the collector 22 and the diaphragms 24, 25, either onto a transparent support, or, for example, forming it as an injection-molded plastic part (PMMA) with a corresponding transparent support edge. The light rays that pass through the plano-convex lens 23 produce the red-reflex illumination, while the light rays that pass through the support or support edge produce the surrounding-field illumination.

It is also advantageous to configure the aperture diaphragm 25 (pin diaphragm) in a particular manner in order to simultaneously produce red-reflex illumination and surrounding-field illumination. An example of this is shown in FIG. 4.

Figure 4:
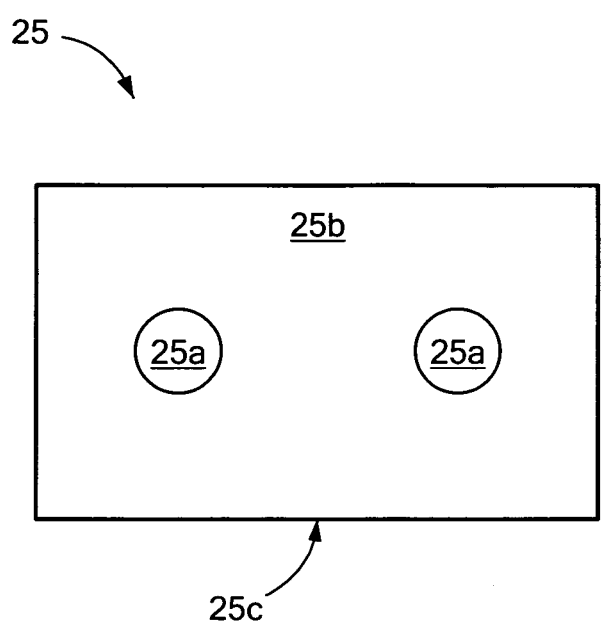
FIG. 4 shows in schematic representation the structure of one advantageous aperture diaphragm, as it is utilized in the illumination device according to FIG. 2.

According to FIG. 4, the aperture diaphragm 25 can be advantageously configured in such a way that the openings 25a for red-reflex illumination can have, for example, a high transmission, while the surrounding region 25b can have a reduced transmission (which is adjustable in the ideal case) for the surrounding-field illumination.

This can be realized, for example, by means of a transmissive or reflective LCD display 25c, or by means of a DMD display.

List of reference numbers

| 10 | Objective element |
| 11 | Means for splitting the illumination light beam |
| 12 | Illumination light bundle |
| 13 | Partial illumination light bundle |
| 14 | Device for changing the cross section of the light bundle |
| 20 | Illumination device |
| 21 | Light guide |
| 22 | Collector |
| 23 | Plano-convex lens |
| 24 | Luminous-field diaphragm |
| 25 | Aperture diaphragm |
| 25a | Opening |
| 25b | Surrounding region |
| 25c | Display |
| 26 | Optical component |
| 27 | Deflecting element |
| 28 | Objective element |
| 29 | Eye |
| 30 | Fundus |
| 31 | Visual field |

What is claimed is:

1. An illumination device for an observation device having one, two or more observation beam paths, having an observation light bundle for each path, having at least one light source for producing at least one illumination light bundle for illuminating an eye to be observed, hereby characterized in that the size of the lighting spot(s) on the fundus of the eye to be observed does not exceed 1× of the cross-sectional area of the observation light bundle on the fundus and in that the at least one illumination light bundle runs coaxially to the corresponding observation light bundle.

2. An observation device, in particular, an operating microscope, having one, two or more stereoscopic observation beam paths, having an observation light bundle for each path, and having an illumination device, having at least one light source for producing at least one illumination light bundle for illuminating an eye to be observed, hereby characterized in that the illumination light bundle forms at least one lighting spot on the fundus of the eye to be observed and that the size of the lighting spot(s) on the fundus does not exceed 1× of the cross-sectional area of the observation light bundle on the fundus and in that the at least one illumination light bundle runs coaxially to the corresponding observation light bundle.

3. The illumination device according to claim 1, wherein the size of the lighting spot(s) on the fundus of the object to be observed does not exceed 0.7× of the cross-sectional area of the observation light bundle on the fundus.

4. The illumination device according to claim 1, wherein the size of the lighting spot(s) on the fundus of the object to be observed does not exceed 0.5× of the cross-sectional area of the observation light bundle on the fundus.

5. The illumination device according to claim 1, wherein the size of the lighting spot(s) on the fundus of the object to be observed does not exceed 0.3× of the cross-sectional area of the observation light bundle on the fundus.

6. The observation device according to claim 2, wherein the size of the lighting spot(s) on the fundus does not exceed 0.7× of the cross-sectional area of the observation light bundle on the fundus.

7. The observation device according to claim 2, wherein the size of the lighting spot(s) on the fundus does not exceed 0.5× of the cross-sectional area of the observation light bundle on the fundus.

8. The observation device according to claim 2, wherein the size of the lighting spot(s) on the fundus does not exceed 0.3× of the cross-sectional area of the observation light bundle on the fundus.

* * * * *